US007016856B1

(12) United States Patent
Wiggins

(10) Patent No.: US 7,016,856 B1
(45) Date of Patent: Mar. 21, 2006

(54) AUTOMATED SYSTEM AND METHOD FOR HEALTH CARE ADMINISTRATION

(75) Inventor: Stephen K. Wiggins, Columbia, SC (US)

(73) Assignee: Blue Cross Blue Shield of South Carolina, Columbia, SC (US)

( * ) Notice: Subject to any disclaimer, the term of this patent is extended or adjusted under 35 U.S.C. 154(b) by 0 days.

(21) Appl. No.: 08/768,029

(22) Filed: Dec. 13, 1996

(51) Int. Cl.
*G06F 17/60* (2006.01)
(52) U.S. Cl. ............................................. 705/2; 705/3
(58) Field of Classification Search ................ 705/2–4, 705/35; 283/54
See application file for complete search history.

(56) References Cited

U.S. PATENT DOCUMENTS

| 4,491,725 A | 1/1985 | Pritchard |
| 4,667,292 A | 5/1987 | Mohlenbrock et al. |
| 4,837,693 A | 6/1989 | Schotz |
| 4,916,611 A | 4/1990 | Doyle, Jr. et al. |
| 4,987,538 A | 1/1991 | Johnson et al. |
| 5,182,705 A | 1/1993 | Barr et al. |
| 5,191,522 A | 3/1993 | Bosco et al. |
| 5,225,976 A | 7/1993 | Tawil |
| 5,235,702 A | 8/1993 | Miller |
| 5,301,105 A | 4/1994 | Cummings, Jr. |
| 5,307,262 A | 4/1994 | Ertel |
| 5,319,543 A | 6/1994 | Wilhelm |
| 5,424,938 A | 6/1995 | Wagner et al. |
| 5,471,382 A | 11/1995 | Tallman et al. |
| 5,523,942 A | 6/1996 | Tyler et al. |
| 5,557,514 A | 9/1996 | Seare et al. |

FOREIGN PATENT DOCUMENTS

EP        0 683 465 A2 * 11/1995

OTHER PUBLICATIONS

Rak, "Where is the Home Care Industry Going ? ", Computers in Healthcare, v7n4 PP:29-34, Apr. 1986, ISSN: 0274-631X, dialog file 15, Accession No. 00314394.*
Jennifer Christensen, *Insuring; the United Service Automobile Associations's Automated Insurance Environment; Success Story,* Oct., 1988, vol. 8; No. 10; p. 47.
John Pallatto, *Expert System Cures the Blues; Blue Cross Develops Insurance Claims Analysis System NERSys,* Dec. 12, 1988, vol. 5; No. 50; p. 35.
Paul Beard, *Blue Cross Develops Insurance Claim ES,* Apr. 1, 1989, vol. 6; No. 7; p. 3.

* cited by examiner

*Primary Examiner*—Frantzy Poinvil
(74) *Attorney, Agent, or Firm*—Barnes & Thornburg LLP

(57) ABSTRACT

An information collection and processing system and related automated method are provided for use by an alliance of organizations providing health care to a given population. The system includes an arrangement for storing information relating to a plurality of contractual relationships existing between the alliance of organizations, a plurality of health care providers, and a plurality of payors (e.g., insurance companies). The storage arrangement also includes a portion for storing information relating to a plurality of patients in the given population, and another portion for storing information relating to transactions between the alliance, the providers and the payors. An aspect of the system and method relates to its capability of storing information relating to an expected receivable resulting from an encounter between a patient and one or more of the providers, storing information relating to a corresponding remittance received as a result of said encounter, comparing the expected receivables with the corresponding remittances, and initiating an action if the remittance falls outside of predetermined limits of the respective receivable. Provisions are made for similar operations involving capitation agreements.

13 Claims, 11 Drawing Sheets

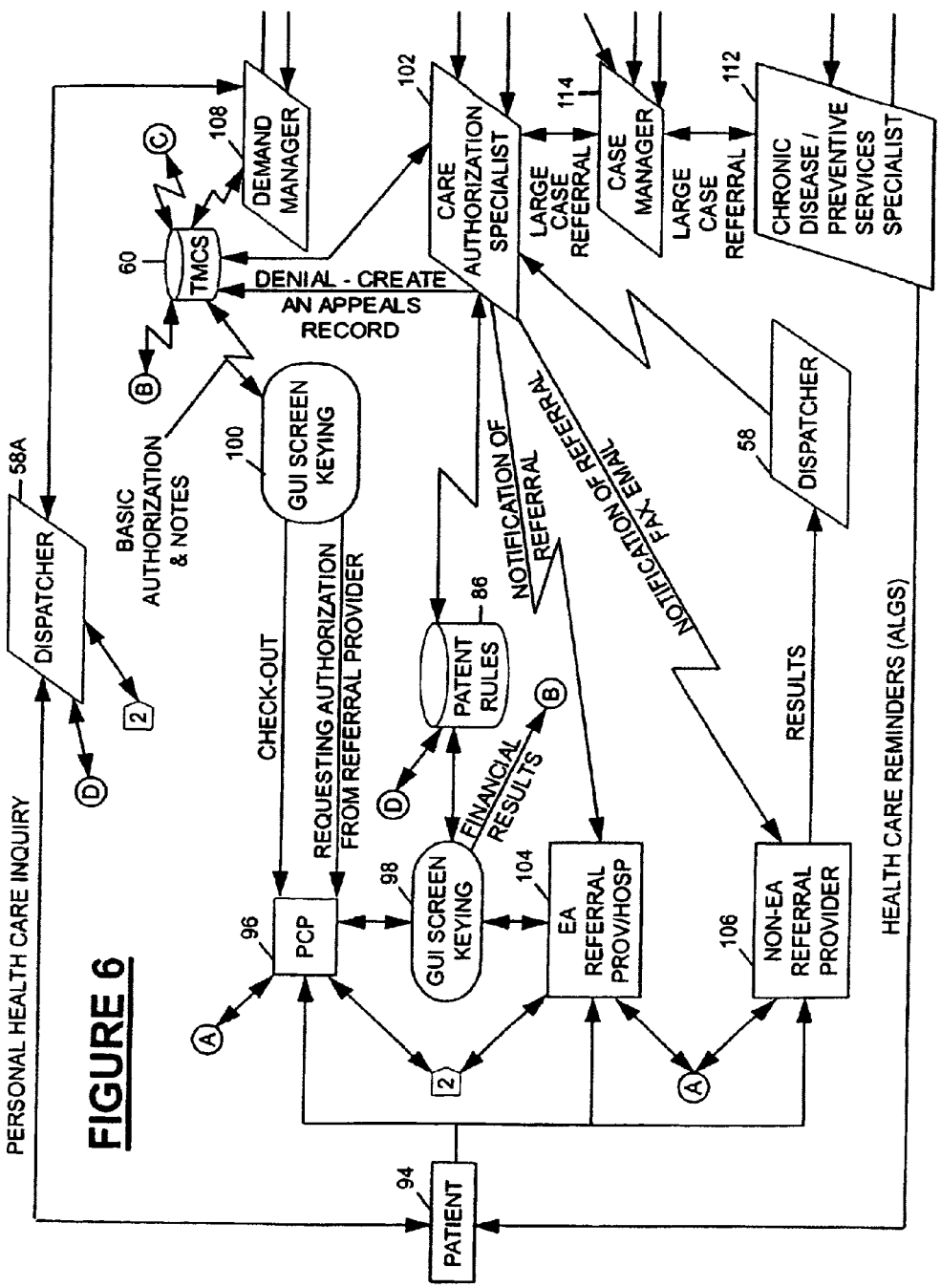

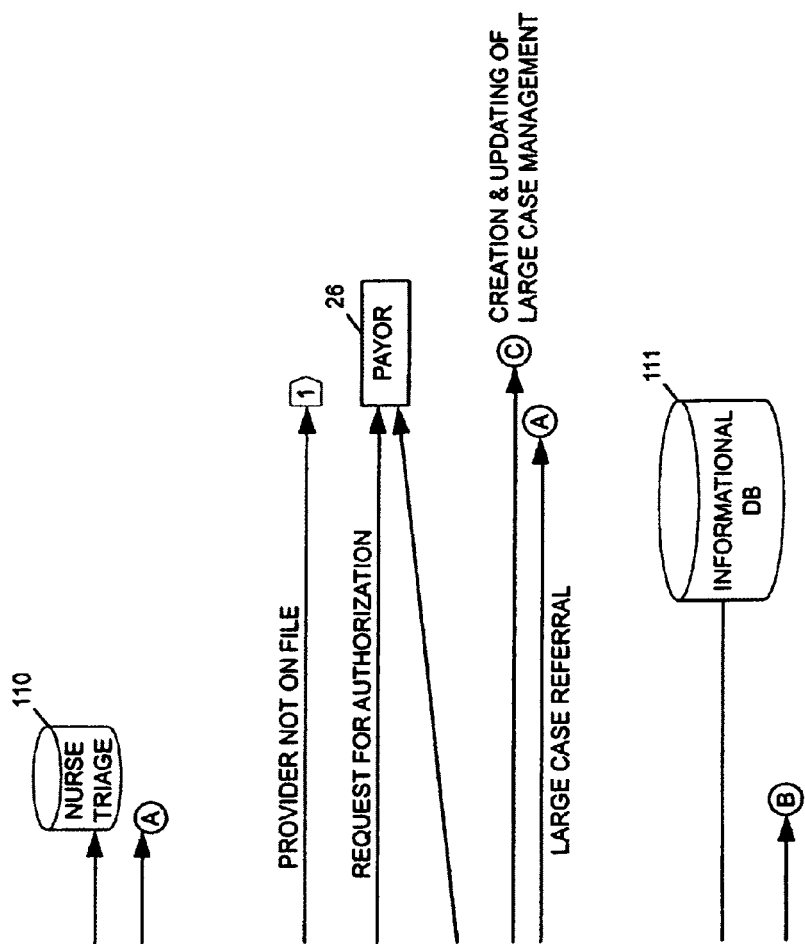

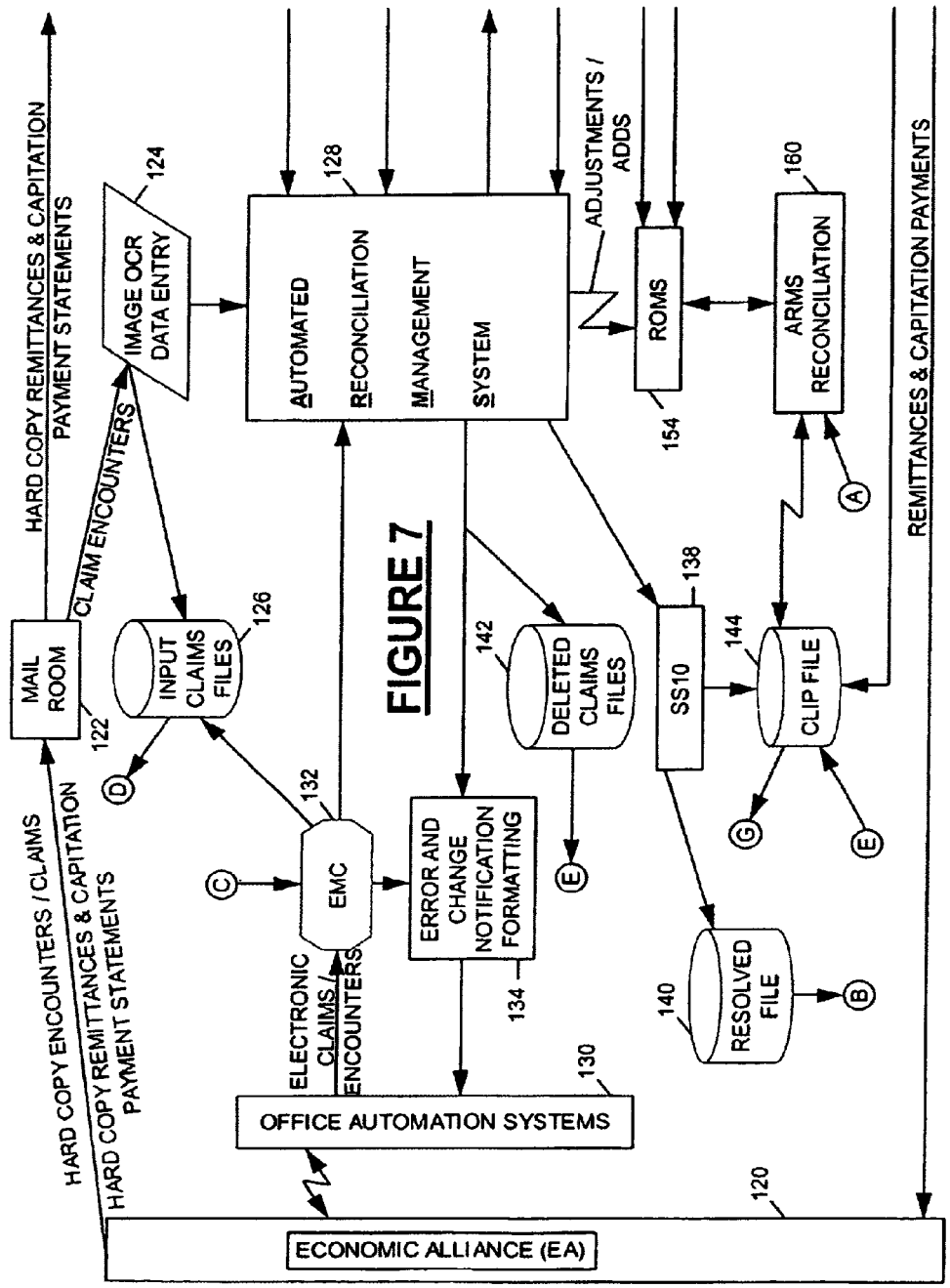

AUTOMATED SYSTEM AND METHOD FOR HEALTH CARE ADMINISTRATION

BACKGROUND AND SUMMARY OF THE INVENTION

The present invention relates generally to an information collection and processing system and an automated method for collecting and processing information. More particularly, the present invention relates to an information collection and processing system and automated method for use by an alliance of organizations providing managed and non-managed health care to a given population.

The advent of managed care in the health care industry has brought substantial changes to the ways participants in the industry deal with each other. These changes are especially apparent in the areas of financial risk and accountability. Through creation of health insurance products based on patient volume, and specific provider networks, insurors have shifted financial risk to physicians, hospitals and other health care service organizations. These changes have occurred while most of the data and administrative tools required to understand and manage such risk have remained with insurors.

In responding to changing industry conditions, physicians, hospitals, and other health care services organizations have formed economic alliances (an "EA") to provide managed and non-managed health care to a given population or geographic area. An EA contracts with multiple insurors to provide managed and non-managed health care to a population under varied reimbursement arrangements, medical practice guidelines, and health plan process requirements. A need exists for automated systems and methods to manage the complex and numerous variables associated with the various arrangements, guidelines, and requirements with which an EA must contend on a day-to-day basis.

It is an object of the present invention to provide automated systems and methods for use by an economic alliance of health care providers and service organizations rendering health care services and providing health care products to a given population.

Another object of the present invention is to provide automated systems and methods for assisting an economic alliance of health care organizations in the management of financial risk inherent in the health care industry.

Yet another object of the present invention is to provide automated systems and methods which allow an economic alliance of health care organizations, as well as individual organizations within the alliance, to more efficiently and effectively deliver health care goods and services under varying reimbursement arrangements, practice guidelines and health plan requirements.

These and other objects are met by an information collection and processing system which comprises an information storage arrangement, a processor for reading and writing information from and to the storage arrangement and for processing such information, and input and output devices for communicating information to and from the processor and the storage arrangement. The information storage arrangement comprises several elements or portions, including a first portion for storing information relating to a plurality of contractual relationships existing between the economic alliance, a plurality of providers of goods and/or services, and a plurality of payors. A second portion of the storage arrangement holds information relating to a plurality of patients in a given population. A third portion of the storage arrangement holds information relating to utilization management functions, demand management functions, catastrophic case management functions, or chronic and preventive services management functions. A fourth portion of the storage arrangement holds information relating to transactions between the alliance, the providers and the payors.

In a preferred embodiment of the invention, information relating to contractual relationships is scanned or imaged into the system. This process may include assigning a unique identifier to elements of information stored in the first portion of the storage arrangement. The unique identifiers are preferably stored in a data base referred to as a provider information management system ("PIMS") data base.

In one embodiment of the invention, the storage arrangement further comprises means for identifying the plurality of providers, payors, or patients by any of a plurality of identifiers by which said providers, payors or patients may be known. This means comprises that portion of the storage arrangement in which a plurality of known identifiers for each of the plurality of providers, payors, or patients are stored.

A preferred embodiment of the invention may also include a capitation data base for storing information relating to capitation contracts, and a rules data base for storing rules relating to system utilization, billing and benefits. An automated letter generating system may also be provided for producing application packages relating to certification or credentialing processes for a provider using information stored in a demographic data base. Computer means for monitoring expiration dates of applicable certification or credentialing information, and for automatically generating a request for updated information, may also be provided.

The storage arrangement may also include means for storing information relating to patient contacts with the alliance, or with one of the plurality of providers in the alliance, in a quality assurance management module of a total managed care system ("TMCS") data base.

In one embodiment of the invention, the information relating to utilization management functions stored in the third portion of the storage arrangement includes information relating to preauthorizations, referral management, and protocol management. The information in the storage arrangement may comprise information relating to claims and encounters, authorizations, health risk assessments and reminder status. This information may be processed to determine a need for generating a case management referral, a disease management referral or an education referral. The system may further comprise means for providing to the providers online access to the generated referrals. This online access may comprise a graphical user interface screen. In addition to referrals, the system of the present invention may also provide means for creating a summary of all patient contacts with the alliance and providers and for providing online access to this summary. This provides the capability of obtaining a quick, complete summary of all contacts a particular patient may have had with the alliance or the providers (or the payors) in a given period of time.

One embodiment of the invention may further comprise means for identifying, within the given population, subpopulations requiring health care information and/or reminders, and means for causing the information and/or reminders to be forwarded to those patients to improve compliance with preventive and disease specific protocols. Information relating to the identification and notification of the subpopulations may be stored in medical management data repository of the TMCS data base.

One embodiment of the invention may further comprise program means for storing information relating to accounts receivables, means for comparing remittances received to amounts expected to be received for respective receivables, and means for initiating a first action if the remittance falls within established tolerances, for example, a predetermined percentage of the respective receivable, and means for initiating a second action if the remittance falls outside of the predetermined percentage of the respective receivable. For instances in which a portion of the population is covered by a capitation agreement, automated means for processing claims relating to transactions covered by the capitation agreement may also be provided. The system may further include means for periodically generating capitation accounts receivables for transactions covered by the capitation agreement, means for comparing respective capitation payments to the accounts receivables, and means for initiating an action if the capitation payments do not fall within a predetermined percentage of the capitation accounts receivables.

The present invention further includes an automated method for use by an alliance of organizations providing managed and non-managed health care to a given population. The automated method comprises the steps of:
 a. storing information relating to a plurality of contractual relationships existing between the alliance, a plurality of providers of goods and/or services, and a plurality of payors;
 b. storing information, including a patient identifier, relating to a plurality of patients in the given population, and a record of encounters between each patient and each provider;
 c. storing information relating to transactions between the alliance, the providers and the payors;
 d. storing a plurality of identifiers for each of the plurality of providers and payors; and
 e. processing the stored information to associate information relating to a particular patient with the patient's identifier, and to associate information relating to a particular provider or payor with each stored identifier for that provider or payor.

In one embodiment of the inventive method, the step of storing information relating to contractual relationships includes storing information relating to such relationships existing between the alliance and a plurality of providers of goods and/or services, the alliance and the plurality of payors, the plurality of providers, and the plurality of providers and the payors. The subject method may also include the steps of assigning a unique identifier to elements of information relating to the contractual relationships, and storing the unique identifiers in the PIMS data base. One embodiment of the invention may also include one or more of the additional steps of:

storing demographic information relating to the alliance, the providers, and the payors in a demographics data base; storing information relating to capitation contracts in a capitation data base; and storing rules relating to system utilization, billing and benefits in a rules data base. The additional step of generating an application package relating to certification or credentialing of a provider using information stored in the demographics data base may also be provided. The method of the present invention may also include the additional steps of monitoring expiration dates of applicable certification or credentialing information, and automatically generating a request for updated information.

In one embodiment of the method of the present invention, the information relating to a plurality of patients comprises rosters obtained from each of the plurality of providers. The invention may also include the additional steps of comparing patient names from the plurality of rosters, and eliminating duplicate names to create a patient master file. The step of storing additional information, including demographic information and health risk assessment data, associated with individual patients in the patient master file to create a customer enrollment system data base may also be included. One embodiment of the invention includes the additional step of storing patient specific rules in a patient rules data base.

One embodiment of the method of the present invention includes the additional steps of storing information relating to communications received from or sent to a patient in the patient master file and in a "tracking" data base which may be part of an activity management system. The method may also include the additional steps of inputting information relating to new patients into the patient master file, and updating the activity management system regarding communications sent to or received from the new patients. The invention may also include the step of allowing providers real time access to information relating to a patient in the patient master file for determination of eligibility status at the time services are provided. Patient rosters from the plurality of providers may be inputted periodically and compared to eliminate duplication and create an updated patient master file.

One embodiment of the method of the present invention includes the step of storing information relating to at least one of utilization management functions, demand management functions, catastrophic case management functions, and chronic and preventive services management functions. Utilization management functions may include preauthorizations, referral management, and protocol management.

An embodiment of the invention may include authorizing referral care, in accordance with information contained in the rules data base, and notifying a referral provider of the referral authorization. In this embodiment, the referral provider may be provided with access to the rules data base.

One embodiment of the method of the present invention may include the additional steps of identifying, within the given population, subpopulations requiring health care information and/or reminders, and causing the information and/or reminders to be forwarded to patients to improve compliance with preventive and disease specific protocols. The subject method may also include the steps of storing information relating to the identification of the subpopulations in a tracking data base. The additional steps of identifying at least one indicator of a potentially high dollar case, and creating a case management record relating to a course of treatment for such case, may also be provided.

One embodiment of the method of the present invention comprises the additional steps of storing information relating to accounts receivables, comparing remittances received to amounts expected to be received for respective receivables, initiating a first action if the remittance falls within predetermined limits of the respective receivable, and initiating a second action if the remittance falls outside of predetermined limits of the respective receivable.

In one embodiment of the invention, at least a portion of the population is covered by a capitation agreement. This embodiment of the present invention may include the additional steps of automatically processing claims relating to transactions covered by the capitation agreement, periodically generating capitation accounts receivables for transactions covered by the capitation agreement, comparing respective capitation payments to the accounts receivables, and initiating an action if the capitation payments do not fall within a predetermined percentage of the capitation accounts receivables.

Other goals, advantages and novel features of the present invention will become apparent from the following detailed description of the invention when considered in conjunction with the accompanying drawings.

BRIEF DESCRIPTION OF THE DRAWINGS

FIG. 6 shows a process flow chart which illustrates elements and process steps of the present invention relating to medical management functions.

DETAILED DESCRIPTION OF THE DRAWINGS

For purposes of the following description, a number of terms should be defined. An "alliance" or "economic alliance" is any group of health care providers who have entered into an agreement to serve a given population of patients. Examples of an economic alliance include a Managed Care Organization ("MCO"), a Physician Service Organization ("PHO"), a Management Service Organization ("MSO"), a multi-hospital system, or other integrated delivery system. A "provider" includes any entity which can provide and bill for health care goods or services provided to a patient. Examples of providers are individual physicians, hospitals, physician groups, physical therapists, ambulatory surgical centers, medical supply vendors, and ambulance services. A "payor" is any insurance company including a Health Maintenance Organization ("HMO"), a Preferred Provider Organization ("PPO") or similar entity), government agency, self-insured employer, third-party administrator, or other entity which directly reimburses providers for services rendered or products provided to patients. Finally, a patient is anyone receiving health care goods or services from a provider, whether that person is a subscriber or member of a particular group, or otherwise.

Figure 1:
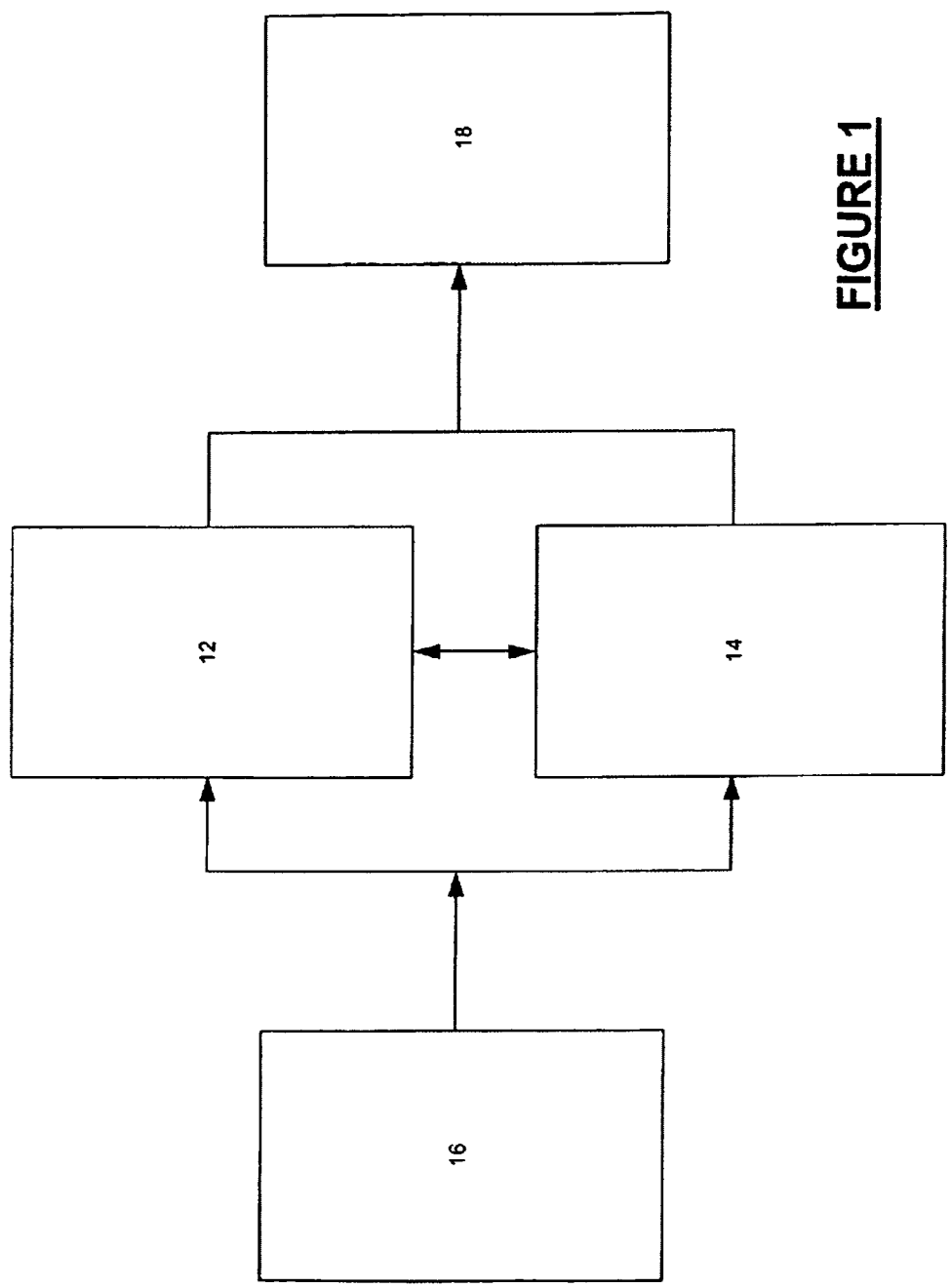
FIG. 1 shows a block diagram of a generalized information collection and processing system in accordance with the present invention.

FIG. 1 shows a block diagram of a generalized information processing system 10 in accordance with the present invention. System 10 comprises a general purpose processor 12, a memory or storage device 14, and an input device 16 and an output device 18 for communicating information to and from processor 12 and storage device 14. It is to be understood that system 10 of FIG. 1 is illustrative only. For example, input device 16 may represent a plurality of devices (keyboards, scanners, imagers, tapes, optical disks, etc.) which can be used to input information or data to processor 12 or storage device 14. Similarly, output device 18 represents any of a plurality of devices (printers, displays, plotters, etc.) used to communicate information from processor 12 or storage device 14 to the system user. Processor 12 is a general purpose computer processor, but is not necessarily limited to types of processors which are currently known and used in the insurance and financial services industry. An example of a processor which can be used to practice the present invention is an Amdahl Model No. 5995-10670.

Storage device 14 is also representative, in a general sense, of various types of information storage devices which may be used to implement the present invention. It is to be understood that the data bases and other memory-related elements and functions discussed below could be implemented in a single storage device, partitioned into portions and subportions or otherwise, or alternatively by a collection of separate storage devices of the same or differing types. The main requirement is that the storage device or devices be able to receive information from and provide information to the input and output devices and the processor, as needed.

Figure 2:
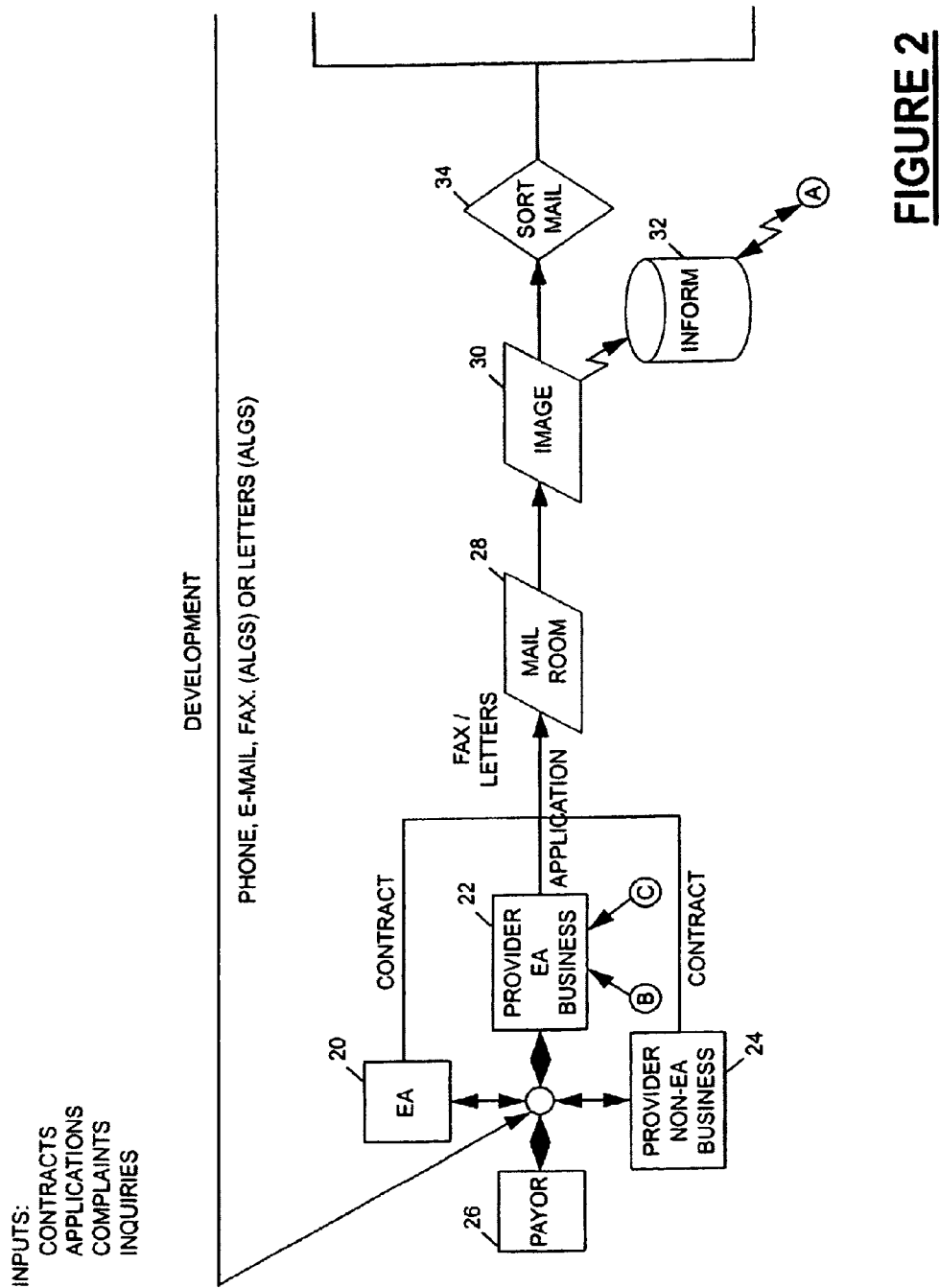
FIG. 2 shows a process flow chart which illustrates elements and process steps of the present invention relating to provider services.
Figure 2:
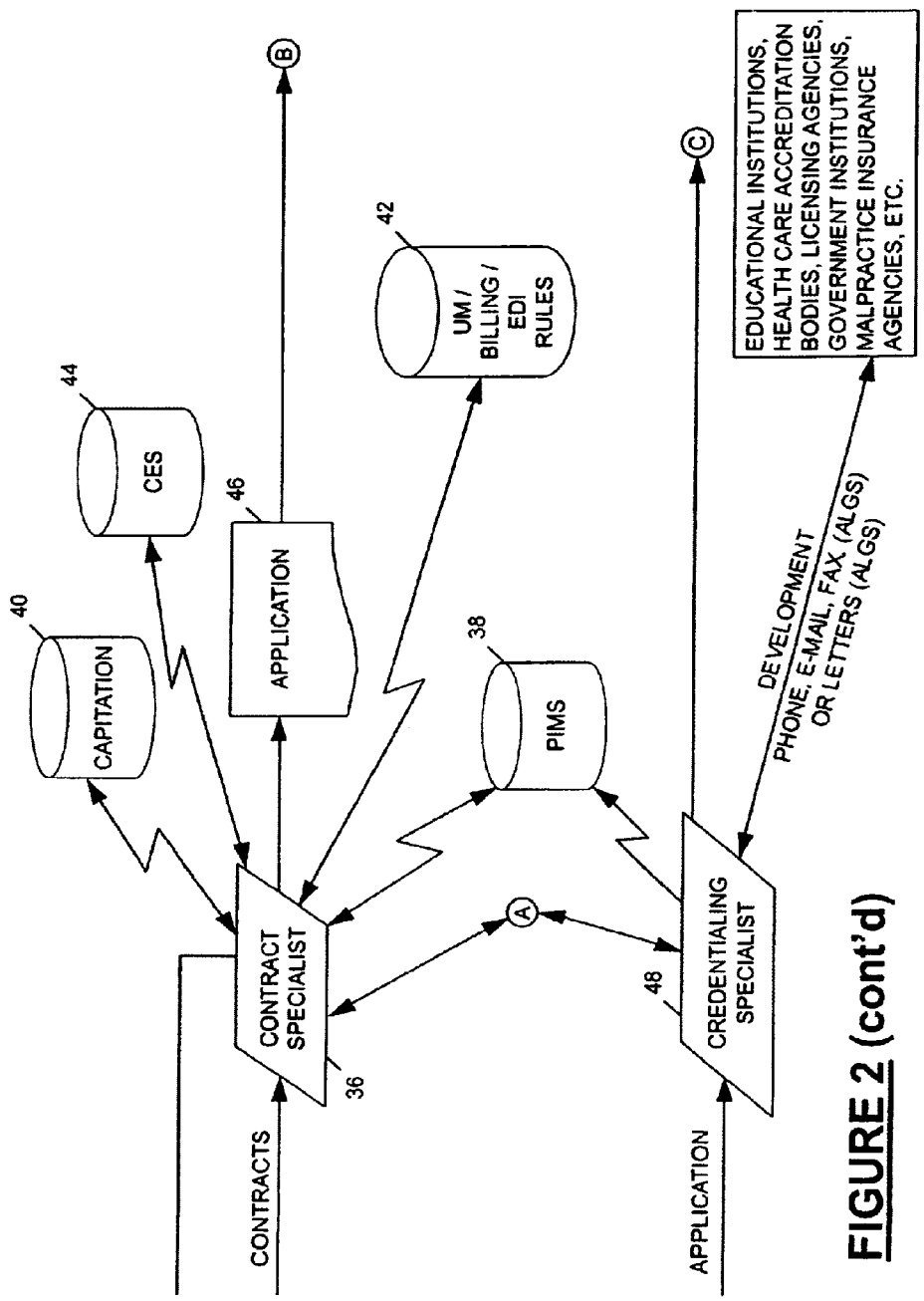

FIG. 2 is a process flow chart which illustrates certain elements and process steps of the present invention. The flow chart of FIG. 2 relates to a portion of the system and method which relates to services to be provided by the invention to and for providers. More specifically, FIG. 2 relates to the initial setup or implementation of the provider services functionality of the subject system and method.

Blocks 20, 22, 24 and 26 represent entities of the types described above. Specifically, Block 22 represents an economic alliance (sometimes referred to below as an "EA") on behalf of whom the information processing system and automated methods of the present invention may be employed. Blocks 22 and 24 represent providers of health care goods and/or services. Block 24 represents that portion of business conducted by providers with other providers or entities who are members of the alliance. Block 24 represents that portion of business conducted by providers which is not alliance related. Block 26 represents payors. As noted above, a payor is typically an insurance company, HMO, PPO, government agency (such as Medicare or Medicaid), self-insured employer, third-party administrator or other entity. The two-way arrows connecting these blocks represents the flow of information or communications among these entities.

The first step in implementing the system or practicing the automated method in accordance with this preferred embodiment of the present invention is the inputting of information relating to contractual relationships. Specifically, information relative to contracts existing between the economic alliance and its providers, the economic alliance and its payors, the providers and other providers, and (for non-economic alliance business) the providers and the payors is inputted into the system. When the system and method of the present invention are used on behalf of a new alliance, much of the information relating to the contractual relationships existing between various parties will be in hard copy document form. Block 28 of FIG. 2 represents a mail room operation at which such documents would be received via mail, fax, or other means. This information would then be scanned or imaged in an operation represented by block 30 and stored in a activity management system 32. A sort operation (represented by block 34) may be performed either before or after the imaging step, as desired.

Activity management system 32 is a system which is capable of managing, monitoring or tracking any multi-step process or ongoing activity. The happening of each step or the occurrence of each event of interest is noted and recorded by the system. Deadlines may be set (either manually or automatically), aged, and monitored. Differing levels of access may be provided to different levels of management. For example, an individual may have access to his or her projects, and can access the system to respond to or determine deadlines, update events, etc. A manager may have a higher degree of access to allow him or her to determine the status of deadlines or progress on projects for those in his or her areas of responsibility. Activity management system 32 may be used to manage multi-step processes, track the status of inquiries (and responses thereto), initiate "workloads" or tasks for forwarding to appropriate personnel, and automatically cause a process to begin (e.g., sending out a welcome package to a new patient) upon the occurrence of another related event (e.g., adding a new patient record to the system).

Each document or pertinent element of information will be assigned a unique identifier (such as a number) prior to storage in a data base referred to as the provider information management system ("PIMS") data base 38. PIMS data base 38 is used to store the information relating to the various contracts and, for tracking purposes, the unique identifiers. The identifiers may be used by other parts of the system in the course of information processing and system operation to track, monitor, recall, associate, and otherwise manage or manipulate the subject information to accomplish the goals of the invention.

The documents relating to the contractual relationships existing between the various entities discussed above may be forwarded to a contract specialist, represented by block 36, following inputting into the PIMS data base 38. The inputted information, along with the unique identifiers, is also made available to the contract specialist for use in operation of the system.

The contract specialist will log the receipt of the documents into activity management system 32 for tracking purposes.

Alternatively, information relating to the contractual relationships may be received electronically, on magnetic storage media, optically, or by other means. Such information is similarly sorted, indexed and stored prior to forwarding to the appropriate contract specialist.

The contract specialist will determine if sufficient alliance, provider and payor demographic data is available from the contract documents to build the PIMS data base represented by element 38. Examples of demographic data of the type stored in PIMS data base 38 include name, provider type (hospital, physician, group practice, etc.), specialty(ies), practice addressees(es), billing address(es), correspondence address(es), electronic mail address(es), telephone numbers (office, business office, facsimile, etc.), point(s) of contact, employer identification number(s), medicare billing number, electronic funds transfer information, category (institution, professional, supplier, etc.), business structure (public, for profit, etc.) and known alias or identifiers used in the industry to refer to each entities. Such information is entered into PIMS data base 38, and the unique identifiers associated with the respective contract documents are linked to provider/payor identification numbers which are assigned to each provider or payor. These identification numbers serve to link all information in the system associated with a particular provider/payor, regardless of the alias used to designate a provider/payor. Following this step, the contract specialist logs the status of the document and respective provider into activity management system 32 for tracking purposes.

If the particular contract relates to a capitated system (i.e., a system which charges a set fee per patient to provide access to health care goods or services), information relating to such agreements is entered into capitation data base 40. Specific rules regarding utilization management, billing, electronic data interchange and other rules of engagement between the alliance, the providers and/or the payors are entered into rules data base 42. Information specific to the alliance is also stored in PIMS data base 38. The contract specialist will continually log the status of the various contractual documents and relationships into activity management system 32 and/or PIMS data base 38 by reference to the unique identifier initially assigned to the contract documents.

If the contract specialist determines that there is not sufficient data available, additional information will be requested by, for example, telephone, or in writing. Where appropriate, an automatic letter generation system ("ALGS") may be used to request additional information. Requests for additional information will be logged into activity management system 32 for tracking purposes. Once the additional information is obtained, the contract specialist will enter the information into PIMS data base 38 as a pending record awaiting credentialing, link the document identification number to the employer identification number, and log the status into activity management system 32 and/or PIMS data base 38. Alliance and payor information will be loaded into data bases 40 and 42 and require no additional actions.

After the demographic information and additional contract information for a provider is successfully loaded into PIMS data base 38, the contract specialist will prompt an automatic letter generating system to generate an application package to the provider for credentialing and/or certification purposes, as appropriate. This operation is represented by block 46. The contract specialist may also notify (by phone, e-mail, fax or letter) the economic alliance of the status of the application. As indicated at (a) in FIG. 2, the contract specialist also initiates an update to activity management system 32 and to a credentialing specialist represented by block 48. Further development of the application (i.e., requests for additional information, responses to inquiries from applicable institutions and agencies, etc.) is the responsibility of the credentialing specialist who communicates as required with the contract specialist as indicated by (a) and the provider as indicated by (c) in FIG. 2. As with other operations, the current status of the credentialing and/or certification process is periodically entered into activity management system 32. Completed applications, attachments, and responses to requests for additional information (when received in document form) will be forwarded to mail room 28 for sorting, imaging, and processing. Each document will be assigned a unique number identifier, and the identifier will be stored in PIMS data base 38. Original documents will be forwarded to the appropriate contract or credentialing specialist who will log the receipt of the documents into activity management system 32.

Credentialing specialist 48 can query PIMS data base 38 to determine a provider's identification number and link imaged documents to that number. The credentialing specialist will determine if all required provider data is present and verified to complete the PIMS record. If additional information is required, the credentialing specialist will contact the appropriate party to obtain the information, and update activity management system 32 with regard to status and required follow-up.

When the credentialing specialist determines that a credentialing and/or certification application is complete, the credentialing specialist reviews and determines if credentialing information requiring source verification can be telephonically verified or must have written verification by the source. In either case, the source is contacted and status information is updated to activity management system 32 and/or PIMS data base 38. When all available information is processed, the credentialing specialist will determine if the verified credentialing information is sufficient to fully activate the provider, or to activate the provider on a temporary basis. In either case, the credentialing specialist will notify the provider and the economic alliance of any change in provider status.

While much of the data used to complete the credentialing/recredentialing or certification/recertification process is stored in PIMS data base 38, it is significant in the preferred embodiment disclosed that activity management system 32 is used to initiate and track these processes.

Following the initial inputting of contract, demographic and other information regarding a group of providers, ongoing provider services will commence. In a preferred embodiment of the invention, ongoing provider services comprise three (3) major subfunctions: (1) new provider and contract loading; (2) provider credentialing/certification; and (3) inquiry tracking. Following is a description of these three major subfunctions. This description will reference the process flow chart of FIG. 3 which incorporates many of the same elements previously discussed and illustrated in FIG. 2. For purposes of clarity, like elements are identified with like reference numerals in FIGS. 2 and 3.

The economic alliance will continually enter into new contractual arrangements and/or agreements with providers and payors. In addition, providers who have entered into contracts with the economic alliance may choose to forward information relating to non-economic alliance business through the system for processing. Accordingly, information relating to contractual arrangements between providers and payors outside of the economic alliance relationships may be inputted into the system. This information will be processed as described above (including assignment of a unique identifier to appropriate documents in PIMS data base 38). Contract specialist 36 will query PIMS data base 38 to determine if the appropriate provider and payor have completed records in PIMS data base 38. If not, the specialist will determine if sufficient demographic data is present to establish a record in PIMS data base 38, and enter base information as a pending record awaiting contract loading and credentialing. The information will be linked to the provider identification number, and the status will be logged into activity management system 32 and/or PIMS data base 38. Payor records will require no further action.

When both the provider and payor have completed records in PIMS data base 38, the contract specialist will determine if there is sufficient contract information to enter the contract into PIMS data base 38. If so, the contract information will be entered as a pending record awaiting verification/credentialing, and the status will be logged into activity management system 32 and/or PIMS data base. If either the provider or contract information is lacking, the contract specialist will obtain the information by telephone or in writing, continually updating the data in PIMS data base 38. Written correspondence will be generated through ALGS, where applicable. Once sufficient information is obtained, the contract specialist will enter the information into PIMS data base 38, and update the status on activity management system 32.

When the base provider information and contract information is successfully inputted into PIMS data base 38, the contract specialist will prompt ALGS to generate an application package for forwarding to the provider for credentialing and/or certification purposes. In addition, a status update will be generated via letter, facsimile or e-mail to the economic alliance. The providers will complete the credentialing and/or certification applications. Credentialing and certification are similar in that both require the completion of an application and the forwarding of licensure, education, and insurance documentation. Credentialing differs from certification in that the credentialing process requires more detailed education and licensure information, and source verification of that information. Certification, in most cases, requires only that copies of documentation be forwarded, recorded and retained on file by the certifying entity.

Completed applications, attachments and responses to requests for additional information will be forwarded (typically, but not exclusively in paper form) to the system user for processing. Upon receipt in mail room 28, these documents will be imaged and sorted and assigned a unique identifier for tracking purposes. The original documents will then be forwarded to the credentialing specialist who will update PIMS data base 38 as the credentialing or certification process progresses.

Figure 3:
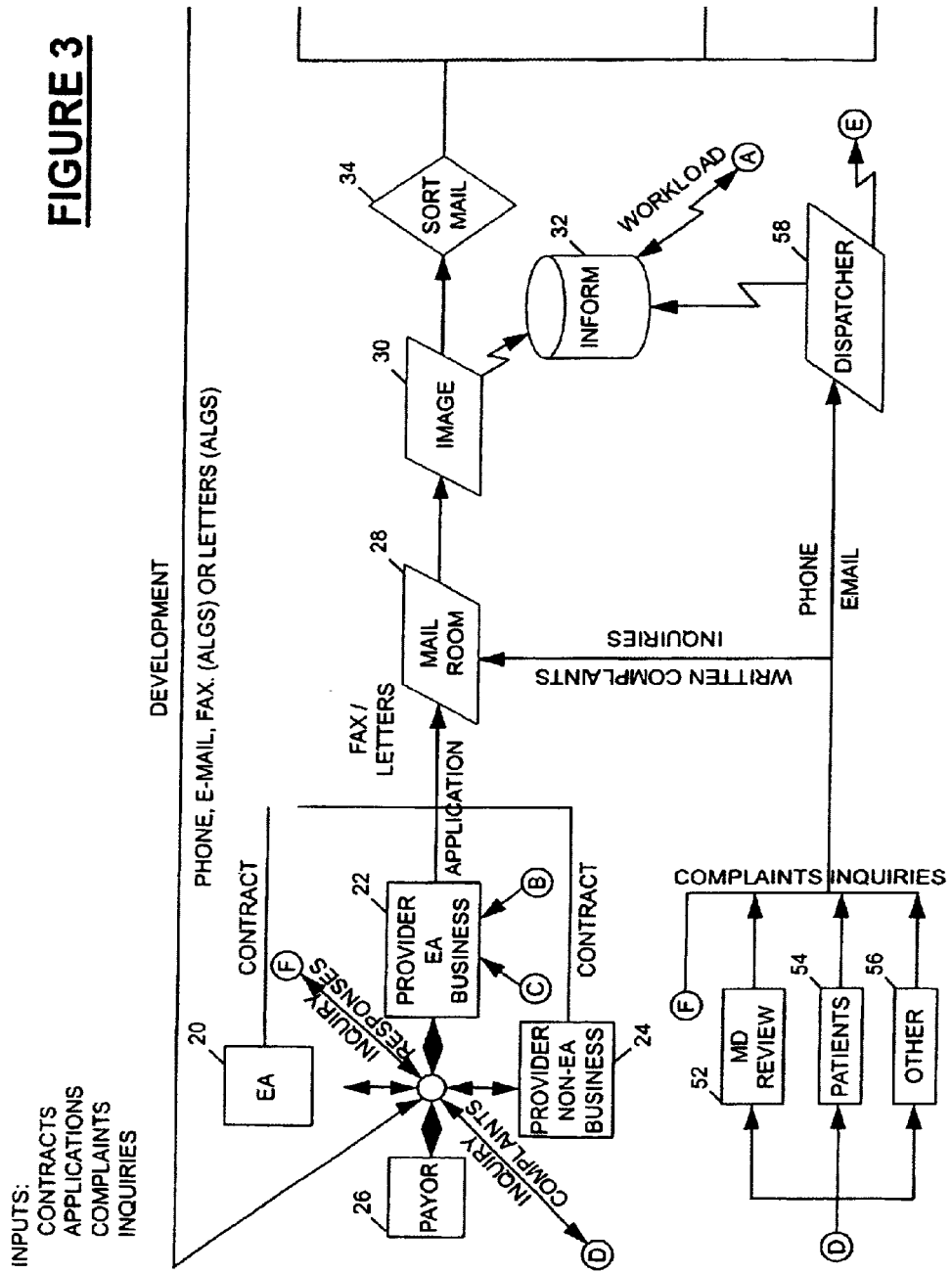
FIG. 3 shows a process flow chart which illustrates elements and process steps of the present invention also relating to provider services.
Figure 3:
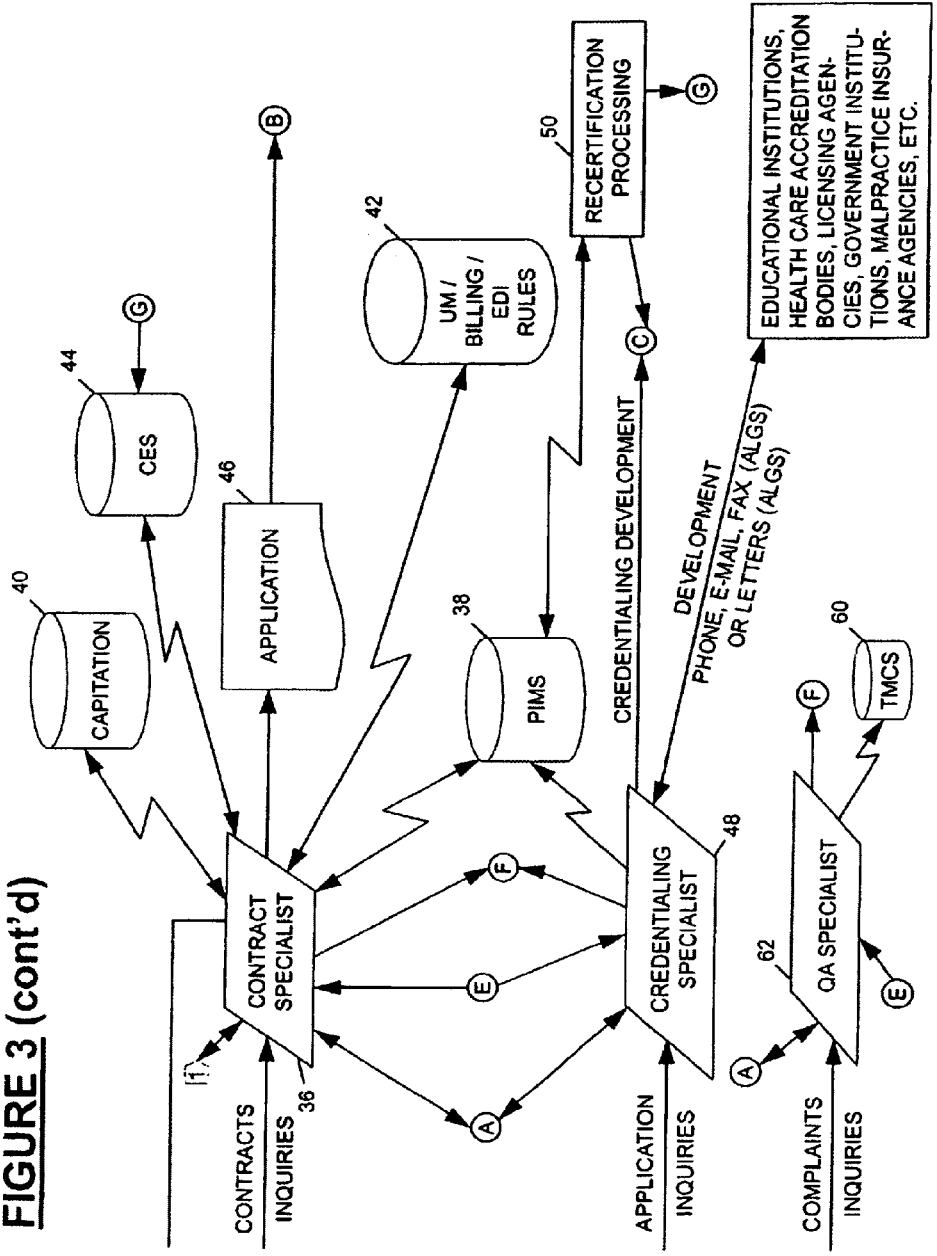

The system and method of the present invention will actively monitor expiration dates of all applicable credentialing and certification information. When dates of expiration are within a predetermined interval, an ALGS letter to the provider requesting updated information will be generated. This process is represented in FIG. 3 by block 50. Upon receipt of updated information, appropriate steps may be taken to maintain certification or credentialing, as necessary.

Inquiries regarding the provider services function can be generated from a number of sources for a number of reasons Sources of inquiry are represented in FIG. 3 by blocks 52, 54 and 56. Regardless of the source, inquiries are handled in a uniform way.

Inquiries are divided into two categories: (1) status requests; and (2) complaints. Either category of inquiry may be received in written form (e.g., letter or facsimile), telephonically, by e-mail or otherwise. All telephonic and e-mail inquiries will be received by a central dispatching center represented by block 58 in FIG. 3. The dispatcher will log inquirer information into activity management system 32, determine the functional area of the inquiry and transfer the inquiry to the appropriate specialist. The specialist will log receipt of the inquiry into activity management system 32.

The receipt and resolution of complaints about medical care, customer service, fraudulent practices, etc. associated with providers having contractual relationships with the alliance are handled in much the same way as status queries, with the exception of distribution of and access to complaint inquiries. All telephonic and e-mail complaints are received by the central dispatcher (58). Due to the sensitive nature of complaints, the dispatcher will route complaints to a quality assurance specialist for investigation. The source may be a patient, another provider, the alliance, a government board or agency, medical oversight board, medical review organization, or other source. The dispatcher will log caller information into a quality assurance management system module of total managed care system ("TMCS") data base 60, and transfer the telephone call or e-mail to a quality assurance specialist, represented by block 62 in FIG. 3. The quality assurance specialist will review the relevant data relating to the telephone call or e-mail in data base 60, inform the complainant that an investigation will begin and that followup information will be provided, and begin actual investigation of the complaint. If further information is required of the complainant or the provider, the quality assurance specialist will prompt ALGS to generate the appropriate request. When the investigation is complete, the quality assurance specialist will log the status in data base 60 and generate a resolution update to the complainant, the alliance and the provider, as appropriate.

For status inquiries, the specialist will log the results of the inquiry in activity management system 32 and prompt ALGS to forward a facsimile, letter or e-mail response to the inquirer. For complaints, when the investigation is complete, the quality assurance specialist will log status in TMCS data base 60 and generate a resolution update to the complainant, the alliance, and the provider, as appropriate.

Figure 4:
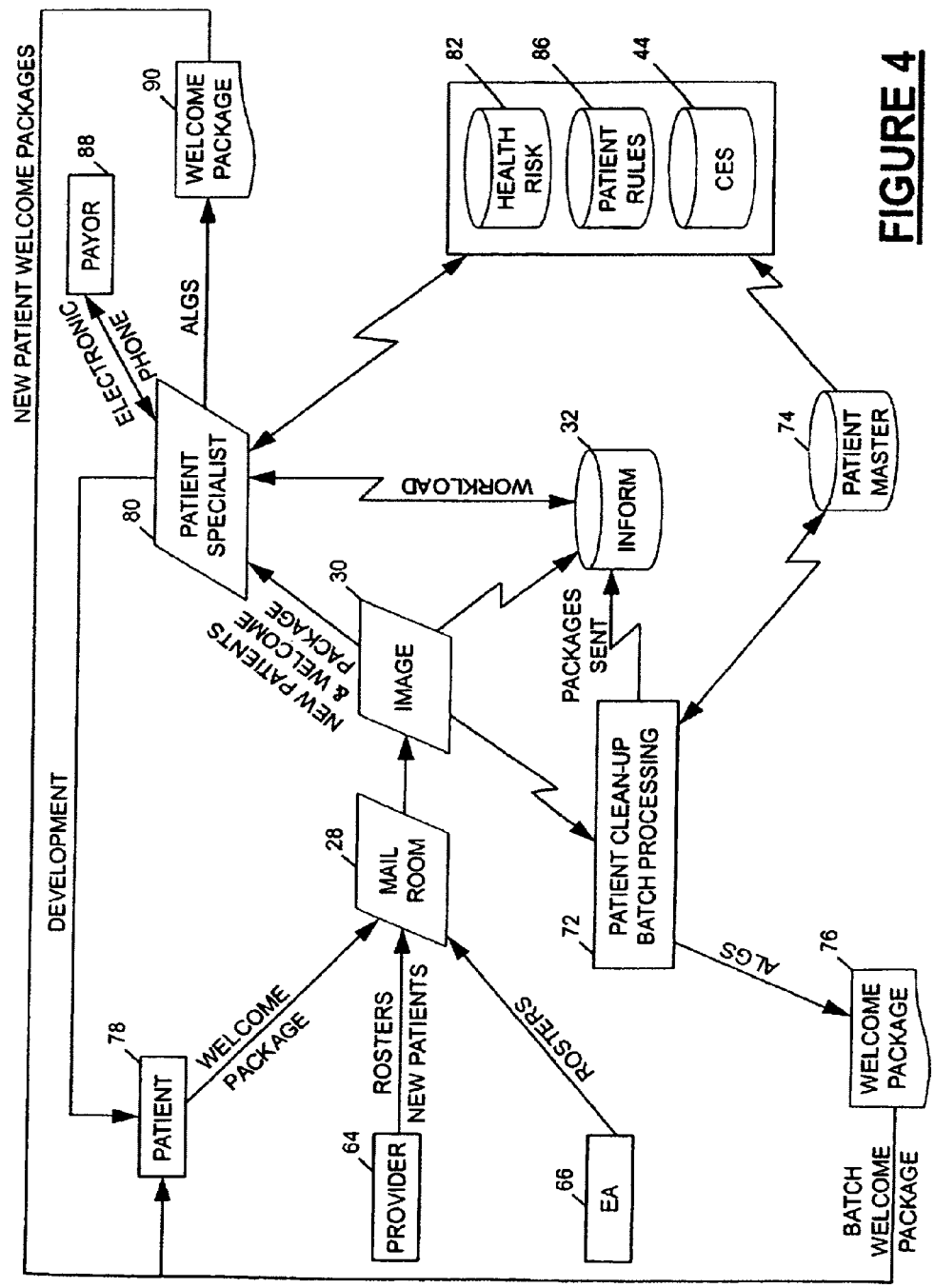
FIG. 4 shows a process flow chart which illustrates elements and process steps of the present invention relating to patient services.

FIG. 4 shows a process flow chart which illustrates elements and process steps of the present invention relating to implementation of patient services functions and features. The first step in implementation of this portion of the system and method is the loading of patient data into the system to enable the alliance to verify eligibility, build patient relationships with payors, and identify any patient specific rules. A base line of patient information must be constructed to facilitate efficient ongoing operations.

The process of loading patient data into the system begins with the obtaining of patient rosters from each provider (or new provider added to an existing system) or alliance (if the system is being used with a previously existing alliance). With reference to FIG. 4, the providers and the alliance are represented respectively by blocks 64 and 66. The provider(s) and/or the alliance will forward rosters to mail room 28 via data, disk, tape, or other means. Rosters in non-electronic form will be forwarded to mail room 28 for imaging or optical character recognition ("OCR") entry (block 30) into a patient clean-up batch processing system represented by block 72. Since the population served by the alliance will typically be located in a distinct geographical area, the potential for patient rosters containing duplicate entries may be relatively high. The patient clean-up batch processing function will identify and delete duplicate entries based on the most current information available. The results of the batch processing will be a patient master file 74 of all patients served by the alliance based on the most up to date information available from the various sources within the alliance.

Upon completion of patient master file 74, welcome packages will be generated by ALGS and forwarded to patients served by the alliance requesting additional demographic information, other health insurance information, and health risk assessment data. This operation is represented by block 76. Distribution of welcome packages will be logged into activity management system 32 for tracking purposes. The patient, represented by block 78 in FIG. 4, will compile the information requested in the welcome package and forward the results to mail room 28 where it will be imaged, or otherwise processed for inputting into the system. The imaging process will create, through entry into activity management system 32, a "workload" or assigned task for a patient specialist (represented by block 80), and the hard copy package will be forwarded to the patient specialist for quality assurance of automated entry and keying of additional data, as appropriate. The patient specialist will enter and/or verify health risk appraisal information on health risk appraisal data base 82, enter patient demographic and other health insurance data and primary care provider relationships on customer enrollment system ("CES") data base 44, and enter any patient specific rules on patient rules data base 86. If data is incomplete or inconsistent, the patient specialist will investigate errors with the patient and/or the appropriate payor (block 88) to obtain or verify information for data bases 82, 84, and 86, recording all interactions with patient 78 or payor 88 in activity management system 32.

During the process of implementing the system, providers within the alliance may encounter new patients within their practices. In that event, basic information regarding these new patients will be forwarded to mail room 28 and imaged or otherwise processed for inputting into the system. Activity management system 32 will be updated to create a work load for the patient specialist, and any hard copy information associated with the work load will be forwarded to the patient specialist. The patient specialist will acknowledge receipt of the information (which will be logged into activity management system 32) and query patient master file 74 to determine if the patient is new to alliance as a whole. If the patient is not new to the alliance (i.e., if a record for this patient exists in patient master file 74) the patient specialist will close out the work load and log this information into CES data base 44. If the patient does not have a record in patient master file 74, a welcome package (90) will be forwarded to the patient, and activity management system 32 will be updated in anticipation of the receipt of a response from the new patient. The use of activity management system 32 to monitor, control and track an assortment of tasks and processes is significant in the context of the disclosed preferred embodiment. For example, when a new patient is added to CES data base 44, a record is created in activity management system 32 to begin the process of sending out a welcome package to the new patient. When an eligibility check is requested and eligibility information is not current, a record is automatically created in activity management system 32 to begin the process of checking current patient eligibility. Because activity management system 32 is used with multiple processes, this same system can be consulted to determine the status of multiple processes and tasks ongoing within the system.

Figure 5:
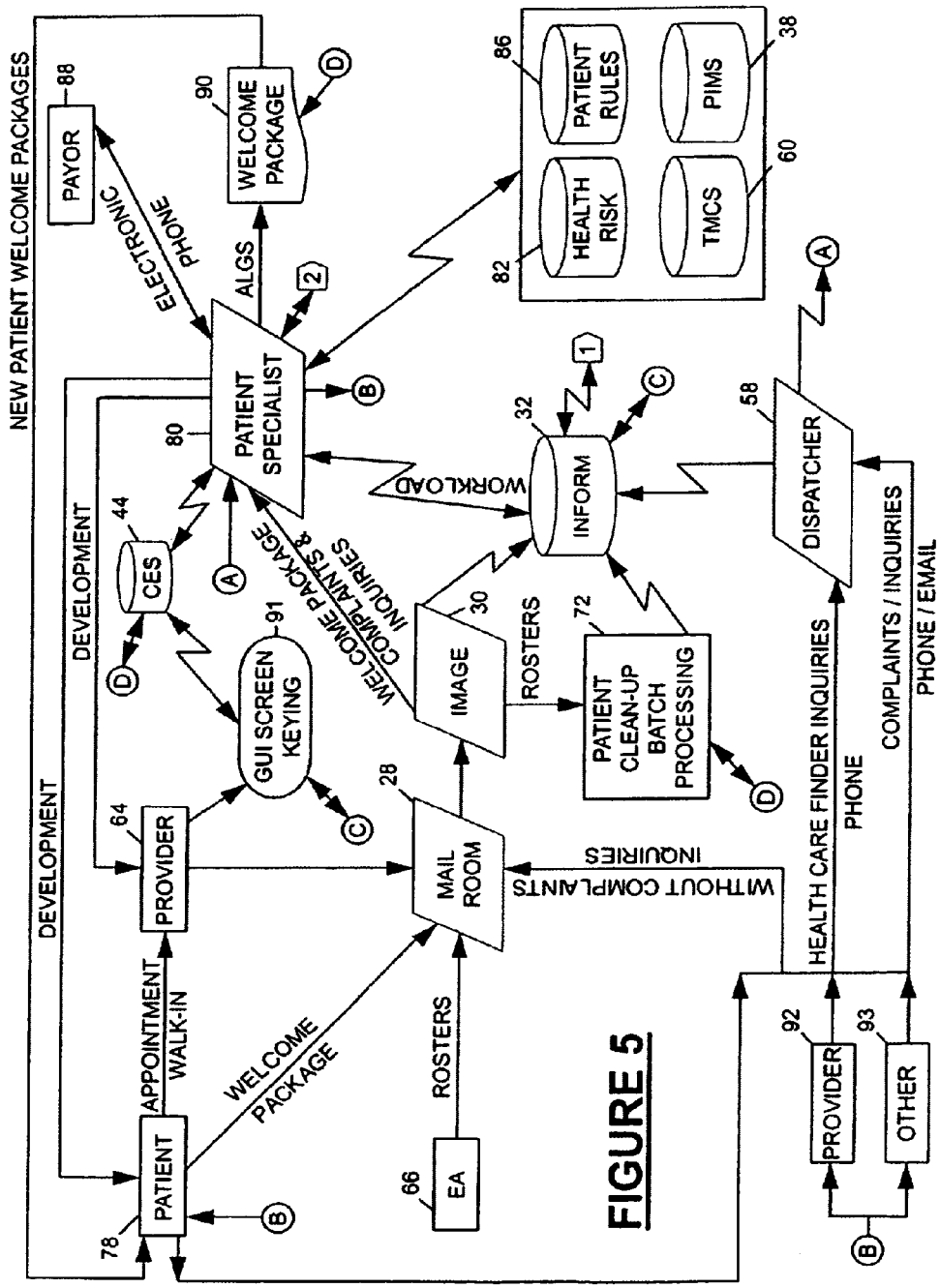
FIG. 5 shows another process flow chart which illustrates elements and process steps of the present invention also relating to patient services.

FIG. 5 illustrates ongoing operation of the patient services component of the preferred embodiment of represented by block 78 in FIG. 5, calls for an appointment or presents themselves to provider (64) for treatment. Provider personnel will enter the patient name or identifier into a graphical user interface ("GUI") screen, represented by block 91, to determine patient eligibility status. The GUI screen will interact with CES data base 44. If the patient is located in CES data base 44, and is otherwise eligible for treatment by the subject provider, the system will provide information from CES data base 44 regarding patient demographic data, insurance information, and eligibility status, to the provider via GUI screen 91.

If the patient is located in CES data base 44, but the eligibility is outside of the payor eligibility time constraints, the system will relay patient demographic data, insurance coverage information, the last verified date and a response back to the provider that eligibility is being verified. At the same time, the system will create a work load within activity management system 32 for the patient specialist which is prioritized appropriately under the circumstances. For example, the highest priority may be assigned to a patient who is in the office of a provider seeking a relatively high cost treatment. In such an instance, a telephone, fax, or e-mail update as to eligibility status may be requested and provided prior to treatment. The next level of priority may be a patient who is present in the office of a provider and either is being treated, or has been treated, and an updated status is requested prior to patient checkout. Yet another level of priority may be applicable to a patient who has an appointment at some future date. In either event, the patient specialist may interact with payor 26, CES data base 44, and activity management system 32 to obtain and provide the appropriate information to the provider in the time frame available.

If, during patient checkin, the patient is not found in CES data base 44, the system will respond to the provider indicating that such is the case and prompt the provider personnel to enter basic patient demographic and insuror information to enable the system to begin verification and patient updating processes. Upon entry of such information, activity management system 32 will generate a work load to the patient specialist to begin the verification process. The patient specialist will then contact the appropriate payor for eligibility verification, enter a base record to CES data base 44, and forward a welcome package (90) to the patient. If, upon verification with the payor, the patient specialist finds that the patient is ineligible for insurance coverage, this information will be forwarded to the provider in a manner consistent with the priority originally assigned to this patient.

Another circumstance may arise if the patient specialist attempts to add a patient to CES data base 44, and the subject payor is not recognized by the system. If this occurs, the patient specialist will forward a workload, via activity management system 32, to contract specialist 36, requesting that the subject payor be added to PIMS data base 38. When this has been accomplished, contract specialist 36 will refer the workload back to patient specialist 80, who will then proceed with the inputting process for this particular patient.

As previously described, new patients receiving welcome packages from the patient specialist will complete the registration and health risk assessment information, and forward the completed package to mail room 28 for imaging or further processing as previously described. Working from this information, the patient specialist will ultimately input and/or verify health risk assessment information on health risk appraisal data base 82, will input and/or verify patient demographic or other insurance data, as well as primary care provider relationships (when applicable), on CES data base 44, and will input and/or verify any patient specific rules on patient rules data base 86. If data is incomplete or inconsistent, the patient specialist will investigate the errors with the patient and/or payor to populate all relevant data bases, recording all interactions with these parties on activity management system 32.

On a periodic basis (e.g. monthly), the providers and/or the alliance will forward enrollment rosters to mail room 28 for inputting and processing as described above in connection with FIG. 4. The purpose of this periodic processing is to remove, on a continuing basis, duplicate patients which may be present in the system. After de-duplication, the rosters may be passed through a series of automated edits, and an updated patient master file will be created. The updated file will be compared against CES data base 44, with one of four events occurring:

1. If a patient record is present on CES data base 44 and the primary care provider ("PCP") has not changed, eligibility will be updated for the specified period of time.

2. If a patient record is present on CES data base 44 and the PCP has changed, eligibility will be updated for the specified period of time and the PCP affiliation will be changed.

3. If a patient record is not present on CES data base 44, a base record will be created, PCP affiliation will be noted, and a welcome package will be forwarded to the patient.

4. If a previously enrolled patient does not appear on the updated file, the PCP affiliation and enrollment status will not be updated and an exception report will be generated for verification by patient specialist 80.

If a patient, provider, or other individual or entity calls for appointment coordination for a patient (blocks 92 and 93), the call will be received by dispatcher 58. Dispatcher 58 will update activity management system 32 and forward the call to patient specialist 80. The patient specialist will use a Health Care Finder ("HCF") function of TMCS data base 60 to locate a provider which meets the referring physician and patient criteria. The HCF program will display only appropriate providers within the network of providers associated with the patient's insurance coverage. Once the appointment is coordinated and/or the caller is given the information about the provider(s), patient specialist 80 will update activity management system 32 regarding results of this effort.

FIG. 6 shows a process flow chart which illustrates elements and process steps relating to medical management functions of the present invention. As in the other figures, like reference numbers are used on occasion to identify components or features of the system previously referred to in FIGS. 2–5. Medical management features of the system include utilization management functions, (such as preauthorizations, referral management, and protocol management), demand management functions, incurring functions of a telephone nurse triage system, catastrophic case management functions, and chronic and preventive services management functions.

For purposes of this application, "utilization management" means any mechanism put into place to manage the consumption of health care to appropriate levels based on the use of clinically validated health care protocols, guidelines and/or standards. Utilization management functions include preliminary evaluation, concurrent review, discharge planning for inpatient care, preauthorization, protocol compliance reviews, and referral algorithms. "Demand management" means any mechanism for reducing the inappropriate use of health care services by those seeking health care, or for increasing compliance with a medical regiment by patients with chronic diseases, or for increasing patient satisfaction while avoiding unnecessary provider encounters. An "encounter" is any patient/provider interaction for which a medical record entry is made.

With reference to FIG. 6, one operational scenario may involve a patient 94 presenting themselves for treatment at a PCP 96. The provider's staff queries patient rules data base 86 through GUI screen 98 to determine the patient's cost share responsibilities. If no additional services are required, patient 94 pays a co-payment if appropriate, and departs from the PCP's facility.

If PCP 96 determines that patient 94 needs additional care beyond the PCP's capabilities, or care requiring additional authorization from the patient's payor, the PCP's staff interacts through GUI screen 100 to build a record regarding authorization for those services in TMCS data base 60. The authorization request is forwarded from TMCS data base 60 to care authorization specialist 102 who will interact with patient rules data base 86 to determine what protocols are to be used for the authorization process, and what level of authorization is required (for example, can the PCP authorize the subject treatment, has authorization authority been delegated to the alliance, or must the payor authorize treatment). If required, the care authorization specialist interacts with the payor (represented by block 26) to obtain authorization.

Once an authorization is obtained, care authorization specialist 102 updates TMCS data base 60 with the authorization information and informs the appropriate alliance referral provider, represented by block 104, of the approved referral. Referral provider 104 may ask patient specialist 80 (FIGS. 4 and 5) to coordinate the appointment for them with the patient or, may contact the patient directly. Alternatively, the patient may choose to contact the referral provider directly. When the patient presents for treatment with referral provider 104, the provider staff queries patient rules data base 86 to determine the patient's co-payment responsibilities and other applicable rules. When treatment is completed, referral provider 104 updates TMCS data base 60 through GUI screen 98. The update may include additional requirements or requests for PCP or payor authorization. PCP 96 then authorizes or requests additional authorization as necessary for continued treatment by referral provider 104. Care authorization specialist 102 may again query patient rules data base 86 to determine authorization requirements and coordinate with payors as needed, updating TMCS data base 60 as appropriate. Care authorization specialist 102 provides referral provider 104 with the additional authorizations required for additional treatment, admission or subspecialty referrals.

If a referral requires the services of a provider outside the alliance's network of providers, care authorization specialist 102 will forward necessary information to the non-EA referral provider (represented by block 106). If the provider is not in PIMS data base 38, care authorization specialist 102 creates a workload in activity management system 32 to contract specialist 36 to create a PIMS data base 38 record. After treatment by out-of-network provider 106, results will be forwarded, via dispatcher 58, to care authorization specialist 102 for entry into TMCS data base 60. This process creates a workload to PCP 96 for review and action, if necessary.

If a patient submits a personal health care inquiry (e.g., calls for an appointment or for health information), the dispatcher (58a in FIG. 6) will determine if the request should be routed directly to a health care finder or to demand manager 108. If the patient's rule states that information and appointments must be referred to demand manager 108, then the demand manager will interact with the protocol driven by telephone nurse triage system 110. Demand manager 108 will provide the patient with appropriate advice and results of the call with be relayed through telephone nurse triage system 110 to TMCS data base 60.

If the patient requires only home care advice or health care information, or sufficient home care advice was given to allow time for scheduling an appointment with PCP 96, the results of the call will be posted to TMCS data base 60 as a work load for PCP 96. PCP 96 will be able to review calls received in any given time interval in priority order, print the results off for entry into patient records (if desired), and coordinate followup care as necessary.

If the patient requires emergency treatment or acute care treatment prior to the PCP's availability, demand manager 108 will interact with patient rules data base 86 and appropriate after-hours care protocols to determine the disposition of the call. The patient will be referred to the appropriate acute or emergency care facility based on the rules associated with their coverage and EA priorities.

Although chronic disease management and preventive services are very different elements of a health care system, the functions they perform are similar enough to group them together for purposes of the preferred embodiment of the present invention. Both functions will query the informational data bases created by the provider services, patient services, and reimbursement management (discussed below) functional areas of the system and method of the present invention. These data bases may include data bases 32, 38, 40, 74, 82 and 86, discussed above, are collectively represented in FIG. 6 by data base 111. Preventive services Specialists (block 112) will target subpopulations of patients to be provided health care information and/or reminders to improve compliance with preventive and disease specific protocols. TMCS data base 60 will be updated to reflect the identification and notification of these patients. TMCS data base 60 will then create work loads to the PCP and/or the specialist treating the patients involved to keep them updated about information and reminders provided to their patients.

Throughout the course of a patient interaction with the system, whether it be the PCP, a specialist, health care facility, demand manager 108, care authorization specialist 102, and/or chronic disease/preventive services specialist 112, a potential high dollar case indicator may be triggered. Once triggered, a case manager (represented by block 114) will research the information to determine if the case qualifies for catastrophic case management. If so, case manger 114 will begin a case management record on TMCS data base 60. The case manager then coordinates with payor 26, PCP 96, and patient 94 to develop the most appropriate course of treatment. The course of treatment will consider the health care benefits associated with the patient, exceptions to benefits that may be required by the payor, community resources available at the patient's location, and the individual's family dynamics. If the course of treatment requires referral to specialists, rehabilitation facilities, durable medical equipment suppliers, etc., case manager 114 will locate those participating with the EA, where possible, or outside the EA, if necessary. All transactions will be recorded on TMCS data base 60 for review and concurrence by PCP 96 or other related specialists involved in the treatment.

Figure 7:
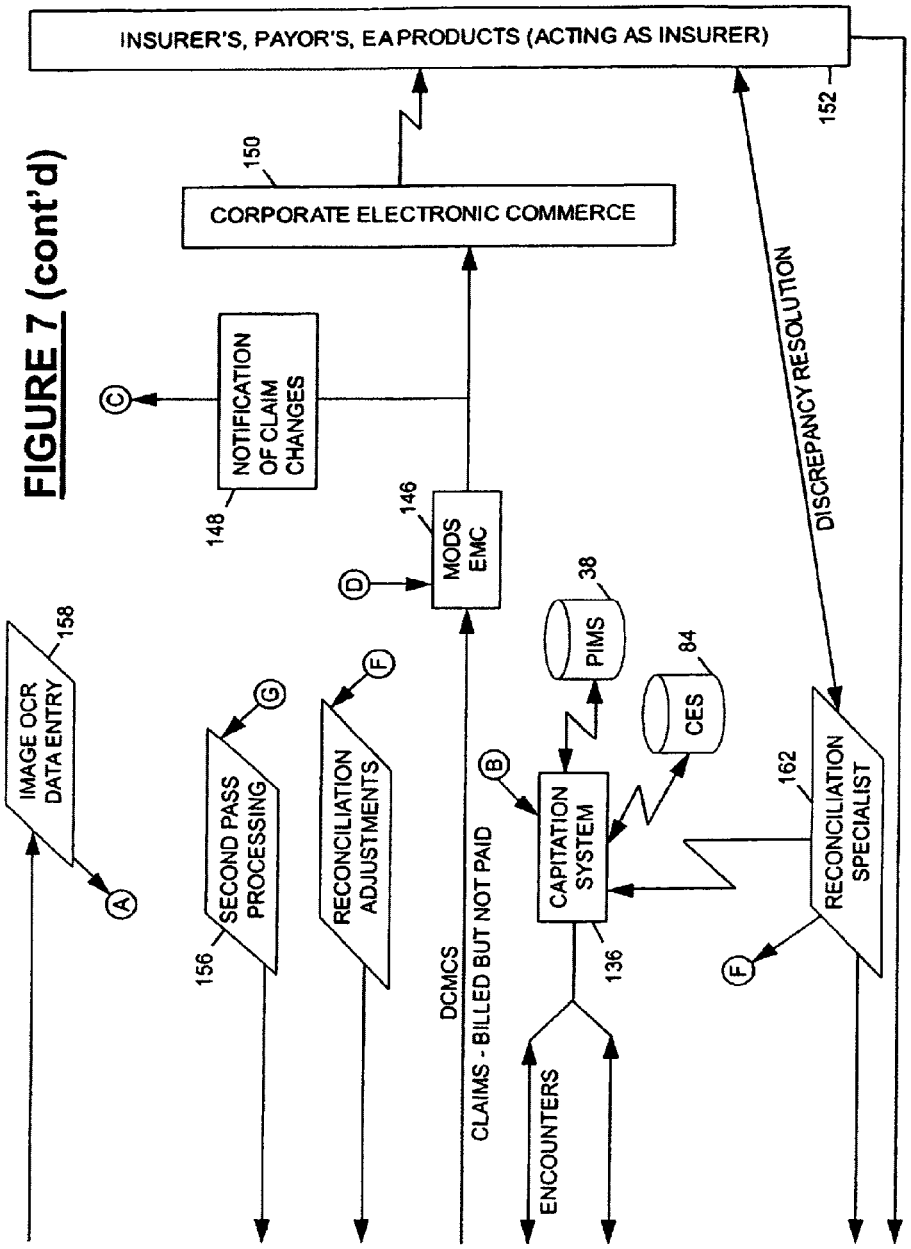
FIG. 7 shows a process flow chart which illustrates elements and process steps of the present invention relating to reimbursement management functions.

FIG. 7 shows a process flow chart which illustrates certain elements and process steps relating to reimbursement management functions of the preferred embodiment of the present invention. Reimbursement management functions include all claims or encounter transactions between a provider of health care goods or services and a payor.

In FIG. 7, the various claim submitting entities (i.e., providers) in the economic alliance are represented by block 120. In the case of submitters or providers who do not have office automation systems or other means to produce electronic claim submissions, hard copy claims will be forwarded to a mail room operation, represented by block 122, for initial handling and sorting. From there, claims will be sent to data entry (block 124) which will typically be accomplished by imaging or OCR techniques. Due to the increasing use of electronic claims submission systems, the number of hard copy claims submitted is not expected to represent a large percentage of total claims. Upon entry of all incoming hard copy claims by data entry personnel, the results of the basic screen edited data will produce input claims file 126 which will ultimately be matched to the output of automated reconciliation management system ("ARMS") 128. This process and its significance is discussed further below. The data entry process will also produce input records for processing by ARMS 128. ARMS 128 is a claims management and adjudication system which has been modified to accept claims from a plurality of providers, price them according to stored contract terms and benefits applicable to one of a plurality of payors, and forward the claims to the appropriate payor.

When claims are received via office automated systems (block 130), basic Electronic Media claims ("EMC") edits will be performed (block 132) and a filing error record (134) will be formatted which can be read by a provider's office automation systems for correction and refiling. The claims that pass through the EMC edits are written to input claims files 126 and forwarded to ARMS 128 for processing. ARMS 128 will separate out claims/encounters which are reimbursed through capitation methodologies and forward them to capitation system 136. Capitation system 136 will verify if the encounter must be submitted to the payor and if the line items on the encounter form are all within the capitation agreement. If encounters are not required to be submitted to a the payor, ARMS 128 will process the encounter through Subsystem 10 ("SS10") (block 138), and write the records to resolved file 140. SS10 138 is a module of the claims processing system which writes the results of the editing process to data bases for analysis and reconciliation. If the encounter data must be forwarded to the payor, ARMS 128 will enter the encounters into the normal claims submission process.

If the capitation encounters contain both capitated and non-capitated line items within the same encounter form, a claims filing error report will be created (134) and forwarded back to the provider for resubmission. At the same time, ARMS 128 will create deleted claims file 142 which will update clip file 144. Clip file 144 is a claims information storage file used to retain information during claims processing. At the completion of processing, the information in clip file 144 is moved to a claims history file. This same process occurs with any claim being processed in which the system detects an error which cannot be corrected by the system or system user personnel, or any error that affects the billed amount.

For claims and/or encounters which pass all of the edits within ARMS 128, the claim/encounter records will be forwarded to a Mods EMC process (represented by block 146), to be matched to input claims file 126. This process is performed to "reattach" data stripped off of the claim/ encounters prior to processing by ARMS 128. Once the claim/encounter is "whole" again, a report will be produced which identifies for the provider any claim/encounter changes which have not affected the billed amount of the claim. This process is represented by block 148. Examples of claim changes which may occur include bundling errors, Current Procedure Terminology ("CPT") Code changes, authorization number identification, etc. The claims are then forwarded to a corporate electronic commerce system (represented by block 150) for printing or electronic distribution to the payors involved, represented in FIG. 7 by block 152. At the same time, ARMS 128 creates an accounts receivable transaction within refund offset monitoring system ("ROMS") 154 and passes claims information through SS10 138 to clip file 144.

Any error which is detected during processing by ARMS 128 which can be edited by the system users staff will cause the claim information to be written to clip file 144, and clip file 144 will generate a work load to a second pass processing area, represented by block 156, for editing and/or correction. These edited claim will be reprocessed through all of the subsystems of ARMS 128, in the same manner as with initially submitted "clean" claims.

Once the payor has adjudicated the claims submitted and a remittance is forwarded to the economic alliance 120, individual providers will update their office automation systems 130. Hard copy remittances are forwarded to mail room 122 for imaging or OCR data entry, (represented by block 158). Remittances will be fed to the ARMS reconciliation process (block 160) which will compare the amount received to the amount expected on ROMS 154. If the remittance is within tolerances set by the EA, ARMS reconciliation process 160 will remove its associated record from clip file 144 and write the completed record to resolved file 140. If the remittance does not match a ROMS 154 record (for example, the payment received was not expected) or it matches a record which was previously closed, ARMS reconciliation process 160 will create a work load which will be forwarded to a reconciliation specialist (block 162) for resolution. Reconciliation specialist 162 will contact the payor and interact with ROMS 154 to identify the error. Once the error is identified, reconciliation specialist 162 will create a record in ROMS 154, if necessary, and forward the claims information for reconciliation adjustment to occur within ARMS 128. This process may create new or modified claims information which will pass through subsystem SS10 138 to update the resolved file. For claims not meeting the designated tolerance, reconciliation specialist 162 will research errors and update ROMS 154 entries to reflect changes in anticipated reimbursement amounts.

At a frequency determined by the various capitation agreements, the encounters within resolved file 140, and information in CES data base 44 and PIMS data base 38 may be used by capitation system 136 to generate an accounts receivable based on the contracts and member accounts on file. The capitated payors will forward the capitation payment to the EA providers, who will forward the capitation statements to mail room 122. Capitation statements will be forwarded by mail room 122 to imaging/OCR data entry, represented by block 158. The capitation information will be inputted to ARMS reconciliation process 160 to be compared to the ROMS 154 entry. If the capitation payment is not within EA tolerances, ARMS reconciliation process 160 will create a work load for the reconciliation specialist who will interact with the payor and capitation system 136 to determine the source of errors in the payment. Reconciliation specialist 162 will make changes as appropriate to capitation system 136 or ROMS 154.

The above-described system allows for the "mining" of data on claims/encounters, authorizations, health risk assessments, and reminder status to determine the need for generating case management referrals, disease management referrals, education referrals, or other referrals or reminders. The results of this process are made available as online workloads, and can be accepted or rejected by clinical staff of the appropriate providers, as deemed appropriate.

The above description of the preferred embodiment refers to one or more rules data bases. Rules data bases may sort any type of information that is not already on a data repository. The system may provide linkage between coded data (diagnostic codes, drug codes, error codes, surgical codes, etc.) with a rule, where appropriate. For instance the system may specify that any head injury diagnoses that appears as part of a claim/encounter in conjunction with specific procedure codes should generate a case management referral. The system may periodically apply various rules to the data contained in the data repository files, or provide that the data mining process will periodically access the rules data bases to apply them to specific types of data. A variety of rules can be created and applied in the system of the present invention.

From the preceding description of the preferred embodiments, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. In an information collection and processing system having a processor, an input arrangement, an output arrangement, and an information storage arrangement, an automated method for use by an alliance of organizations providing managed and non-managed health care to a given population, wherein at least a portion of said population is covered by a capitation agreement, comprising the steps of:

a. storing information relating to a plurality of contractual relationships existing between the alliance, a plurality of providers of goods and/or services, and a plurality of payors;

b. storing information relating to a plurality of patients in the given population, said information including a patient identifier and a record of encounters between each patient and each provider;

c. storing information relating to transactions between the alliance, the providers and the payors;

d. storing a plurality of identifiers for each of the plurality of providers and payors;

e. processing said stored information to associate information relating to a particular patient with said patient's identifier, and to associate information relating to a particular provider or payor with each stored identifier for that provider or payor;

f. periodically generating capitation accounts receivables for transactions covered by said capitation agreement;

g. comparing respective capitation payments to the accounts receivables; and h. initiating an action if the capitation payments do not fall within a predetermined percentage of the capitation accounts receivables.

2. An automated method according to claim 1, further comprising the steps of assigning a unique identifier to elements of information relating to said contractual relationships, and storing the unique identifiers in a data base.

3. An automated method according to claim 1, further comprising the additional step of storing demographic information relating to the alliance, the providers, and the payors in a demographics data base.

4. An automated method according to claim 3, further comprising the additional step of generating an application package relating to certification or credentialing of a provider using information stored in the demographics data base.

5. An automated method according to claim 4, further comprising the additional steps of monitoring expiration dates of applicable certification or credentialing information, and automatically generating a request for updated information.

6. An automated method according to claim 1, comprising the additional step of storing information relating to capitation contracts in a capitation data base.

7. An automated method according to claim 1, comprising the additional step of storing rules relating to system utilization, billing and benefits in a rules data base.

8. An automated method according to claim 1, further comprising the additional steps of identifying, within the given population, subpopulations requiring health care information and/or reminders, and causing said information and/or reminders to be forwarded to patients to improve compliance with preventive and disease-specific protocols.

9. An information collection and processing system for use by an alliance of organizations providing managed and non-managed health care to a given population, wherein at least a portion of said population is covered by a capitation agreement, comprising:

an information storage arrangement having:

a. a first portion for storing information relating to a plurality of contractual relationships existing between the alliance, a plurality of providers of goods and/or services and a plurality of payors;

b. a second portion for storing information relating to a plurality of patients in the given population;

c. a third portion for storing information relating to at least one of:

1. utilization management functions;
2. demand management functions;
3. catastrophic case management functions; and
4. chronic and preventive services management functions; and d. a fourth portion for storing information relating to transactions between the alliance, the providers and the payors;

a processor for reading and writing information from and to the storage arrangement, and for processing said information;

an input device and an output device for communicating information to and from the processor and the storage arrangement;

automated means for processing claims relating to transactions covered by said capitation agreement; and further comprising means for periodically generating capitation accounts receivables for transactions covered by said capitation agreement, means for comparing respective capitation payments to the accounts receivables, and means for initiating an action if the capitation payments do not fall within a predetermined percentage of the capitation accounts receivables.

10. An information collection and processing system according to claim 9, further comprising means for assigning unique identifiers to elements of information stored in the first portion of the storage arrangement, and for storing the unique identifiers in a data base.

11. An information collection and processing system according to claim 9, further comprising means for identifying said plurality of providers, payors or patients by any of a plurality of identifiers by which said providers, payors, or patients may be known.

12. An information collection and processing system according to claim 9, further comprising means for storing a summary of patient contacts with the alliance and the providers in a data base, and for providing online access to the summary.

13. Apparatus for administering a health care system, comprising;

an information storage arrangement having:

a. a first portion for storing information relating to a plurality of contractual relationships existing between an alliance of health care providers, and a plurality of payors;

b. a second portion for storing information relating to a plurality of patients in a given population, said information including a patient identifier and a record of encounters between each patient and one or more of the providers;

c. an input claims file for storing a plurality of claims from one or more of the providers, d. a third portion for storing information relating to an expected receivable resulting from each respective encounter; and e. a fourth portion for storing information relating to corresponding remittances received as a result of each encounter;

a processor for reading and writing information to and from the storage arrangement, and for processing said received claims to determine which claims are to be submitted to which of one or more of the payors and for comparing the expected receivables with the corresponding remittances;

means for initiating an action if the remittance falls outside of predetermined limits of the respective receivable; and an input device and an output device for communicating information to and from the processor and the storage arrangement; and wherein at least a portion of the population is covered by a capitation agreement, and further comprising means for periodically generating capitation accounts receivables for transactions covered by said capitation agreement, means for comparing respective capitation payments to the accounts receivables, and means for initiating an action if the capitation payments do not fall within a predetermined percentage of the capitation accounts receivables.

* * * * *